(12) United States Patent
Matsumoto et al.

(10) Patent No.: US 7,211,413 B2
(45) Date of Patent: May 1, 2007

(54) PROCESS FOR PRODUCING PURIFIED ANTHOCYANIN AND CRYSTALLINE ANTHOCYANIN

(75) Inventors: Hitoshi Matsumoto, Saitama (JP); Satoshi Hanamura, Saitama (JP); Masao Hirayama, Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 629 days.

(21) Appl. No.: 10/380,056

(22) PCT Filed: Sep. 11, 2001

(86) PCT No.: PCT/JP01/07891

§ 371 (c)(1),
(2), (4) Date: Mar. 11, 2003

(87) PCT Pub. No.: WO02/22847

PCT Pub. Date: Mar. 21, 2002

(65) Prior Publication Data

US 2004/0101933 A1    May 27, 2004

(30) Foreign Application Priority Data

Sep. 12, 2000   (JP) .............................. 2000-276540

(51) Int. Cl.
    *C12P 19/60*    (2006.01)
(52) U.S. Cl. .............................. 435/75; 435/72; 536/8
(58) Field of Classification Search .................. 435/72, 435/75; 536/8
    See application file for complete search history.

(56) References Cited

U.S. PATENT DOCUMENTS

| | | | |
|---|---|---|---|
| 3,546,337 A * | 12/1970 | Chibret ........................ | 514/27 |
| 3,885,149 A * | 5/1975 | Ono ............................ | 504/189 |
| 4,320,009 A * | 3/1982 | Hilton et al. ................ | 210/651 |
| 4,888,173 A * | 12/1989 | Mason et al. ................ | 424/764 |
| 5,447,862 A * | 9/1995 | Heim et al. ................. | 435/252.3 |

FOREIGN PATENT DOCUMENTS

| | | |
|---|---|---|
| EP | 1 208 755 A1 | 5/2002 |
| ES | 2000294 A * | 2/1988 |
| JP | 3-209320 | 9/1991 |
| JP | 3-209321 | 9/1991 |
| WO | WO 98/38316 A1 | 9/1998 |

OTHER PUBLICATIONS

Renault, J et al. Preparative separation of anthocyanins by gradient elution centrifugal partition chromatography. Journal of Chromatography A. 1997. 763: 345-352.*
H. Matsumoto et al., "Preparative-Scale Isolation of Four Anthoxyanin Components of Black Current (*Ribes nigrum* L.) Fruits," in J. Agric. Food Chemistry, V. 49, No. 3, pp. 1541-1545 (2001).

Dictionary of Natural Products, V. 1, A-C, Chapman & Hall, London (1994), pp. 2799, 2800, 3503, and 4542.
Cato Froytlog et al., "Combination of chromatographic techniques for the preparative isolation of anthocyanins-applied on black currant (*Ribes nigrum*)," No. 825, J. Chromatograpy A, pp. 89-95 (1998).
A. Degenhardt et al., "Separation and purification of anthocyanins by high-speed countercurrent chromatography and screening for antioxidant activity," vol. 48, J. Agric. Food Chem., pp. 338-343 (2000).
Ando et al., "Floral anthocyanins in wild taxa of Petunia (Solanacea)," vol. 27, Biochemical Systematics and Ecology, pp. 623-650 (1999).
Ordaz-Galindo Alejandro et al., "Purification and identification Capulin (Prunus Serotina Ehrh) anthocyanins", vol. 65, Food Chemistry, pp. 201-206 (1999).
Rikke Norbaek et al., "Anthocyanins in Chilean Speacies of Alstroemeria," vol. 42, No. 1, Phytochemistry, pp. 97-100, (1996).
J. Millet et al., "Improvement of blood filtrability in cynomologus monkeys . . . ",vol. 15, No. 4, J. Pharmacol. (Paris), pp. 439-445, (1984).
Jean-Hughes Renault et al., "Preparative separation of anthocyanins by gradient elution centrifugal partition chromatography," No. 763, Journal of Chromatography A, pp. 345-352, (1997).
Li, KC et al. The anthocyanin pigments of sour cherries. *Journal of the American Chemical Society.* 1956. 78:979-80.
Wightman, JD et al. Beta-glucosidase activity in juice-processing enzymes based on anthocyanin analysis. *Journal of Food Science.* 1996. 61(3): 544-547.
He, S. et al. Assignment of sweet almond beta-glucosidase as a family 1 glycosidase and identification of its active site nucleophile. *Journal of Biological Chemistry.* 1997.272 (40): 24864-24867.

* cited by examiner

*Primary Examiner*—Leon B. Lankford, Jr.
*Assistant Examiner*—Susan E. Fernandez
(74) *Attorney, Agent, or Firm*—Posz Law Group, PLC; R. Eugene Varndell, Jr.

(57) ABSTRACT

Provided are a process for producing purified anthocyanidin glucoside in which a rhamnose end of anthocyanidin rutinoside is cleaved using rhamnosidase to convert the anthocyanidin rutinoside component into anthocyanidin glucoside, the anthocyanidin glucoside component being then purified and isolated; or a crystalline anthocyanidin glucoside salt obtained by further crystallizing the purified anthocyanidin glucoside and a process for producing the same.

Also provided are a process for producing purified anthocyanidin rutinoside in which a glucose end of anthocyanidin glucoside is cleaved using β-glucosidase to degrade and remove the end, the anthocyanidin rutinoside component being then purified and isolated; or a crystalline anthocyanidin rutinoside salt obtained by further crystallizing the purified anthocyanidin rutinoside and a process for producing the same.

7 Claims, No Drawings

PROCESS FOR PRODUCING PURIFIED ANTHOCYANIN AND CRYSTALLINE ANTHOCYANIN

TECHNICAL FIELD

The present invention relates to a process for producing purified anthocyanin from anthocyanin derived from natural product and a process for producing crystalline anthocyanin by further crystallizing purified anthocyanin, and a crystalline anthocyanin prepared by the aforementioned process.

More particularly, the present invention relates to a process which facilitates the subsequent purification and crystallization steps by enzymatically converting or removing anthocyanidin rutinoside or anthocyanidin glucoside constituting anthocyanins to decrease anthocyanidin rutinoside or anthocyanidin glucoside.

BACKGROUND ART

Anthocyan is a generic term for anthocyanidin, which has a backbone represented by the following formula (I), in combination with anthocyanin, which is a glycoside formed by binding of saccharide to anthocyanidin.

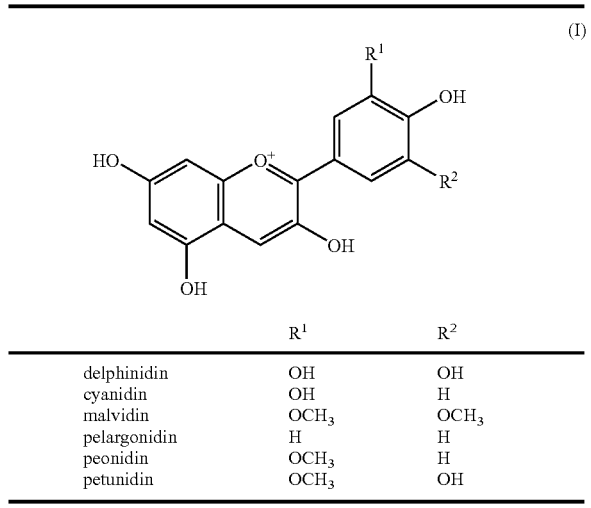

(I)

|  | $R^1$ | $R^2$ |
|---|---|---|
| delphinidin | OH | OH |
| cyanidin | OH | H |
| malvidin | $OCH_3$ | $OCH_3$ |
| pelargonidin | H | H |
| peonidin | $OCH_3$ | H |
| petunidin | $OCH_3$ | OH |

Examples of anthocyanidin, i.e., an aglycon, include delphinidin, cyanidin, malvidin, pelargonidin, peonidin, and petunidin. Anthocyanin is referred to as anthocyanidin glucoside when, for example, glucose is bound to the anthocyanidin as a glycoside. Saccharide found in anthocyanin includes: monosaccharide such as galactose and arabinose in addition to glucose; and disaccharide such as rutinose and sophorose.

Anthocyans are widely present in nature, and are mainly used as a natural pigment for food or, because of their functionalities, are extensively used for pharmaceuticals, quasi drugs, cosmetics, and the like in Europe. For example, use thereof as a cicatrizant, as disclosed in Japanese Examined Patent Publication (Kokoku) No. 59-53883, or pharmacological properties thereof which are valuable in the treatment of peripheral blood diseases using anthocyanin derived from blueberry, as disclosed in Japanese Laid-open Patent Publication (Kokai) No. 3-81220, have been discovered. In recent years, the functionality of anthocyanin has drawn attention in Japan for uses of anthocyanin other than as a pigment. The present inventors have also found several useful efficacies in anthocyanin of black currant and these are reported in WO 01/01798.

When these anthocyanins having pharmacological properties are used as pharmaceuticals and the like, highly purified ones are required. Heretofore, however, mass production of highly purified anthocyanins has never been realized. Further, while highly purified anthocyanins are preferably crystalline from the viewpoint of stability, hygroscopicity, and the like, mass production of crystalline anthocyanins has likewise not been realized up to now.

Conventionally, anthocyanin compositions for pharmaceuticals are mainly preparations derived from blueberry with an anthocyanin content of 25% by weight or lower. Thus, at least several hundred mg of an anthocyanin preparation had to be administered per dose in order to exhibit its effectiveness, and the consumption of a small amount thereof could not produce pharmacological effects in practice. Accordingly, compositions containing highly purified anthocyanin at high levels have been awaited.

Highly purified anthocyanin was not present because of the following reasons. For example, in the case of blueberry-derived anthocyanin, there are 15 types of anthocyanin components, and the physiochemical properties of these substances are very similar to one another. Thus, the respective flux peaks thereof overlap with one another in purification using a preparative column or the like. Or, separation and purification were impossible because each component was in a very small amount.

In the case of anthocyanin derived from black currant, for example, four components, i.e., cyanidin-3-O-glucoside (hereinafter it is abbreviated to "C3G"), cyanidin-3-O-rutinoside (hereinafter it is abbreviated to "C3R"), delphinidin-3-O-glucoside (hereinafter it is abbreviated to "D3G"), and delphinidin-3-O-rutinoside (hereinafter it is abbreviated to "D3R"), are contained as anthocyanins. As with the blueberry-derived anthocyanin, due to very similar physiochemical properties among the four substances, even mixtures of these four components have very close chromatography peaks. Even if preparative chromatography or centrifugal partition chromatography were performed to obtain purified anthocyanin, mass production thereof was impossible due to extremely deteriorated yield. The quantitative ratio of representative anthocyanins in black currant is as follows: D3G, D3R, C3G, and C3R are respectively present at 12.5%, 47.9%, 4.1%, and 35.5%. Consequently, purification of a large amount of D3G and C3G components, which are contained at low levels, involved further difficultly, and thus a process for mass producing purified anthocyanin has been awaited.

In contrast, anthocyan has been heretofore known to have a drawback in its stability. The present inventors have applied for patent on a process for stabilizing substances containing anthocyanin at high level by adding phytic acid, saccharides, and sugar alcohols as stabilizers (PCT/JP00/09204). However, when a large amount of anthocyanin is used for making preparations, there is no room to contain these additives. Accordingly, more stable physical properties were required and preparations using crystalline anthocyanin, which is physically more stable, were awaited. Thus, conventionally, high purity anthocyanin was organically synthesized for pharmaceutical applications through many steps by, for example, a process for synthesizing delphinidin hydrochloride (anthocyanidin hydrochloride of an aglycon instead of glycoside) as disclosed in Japanese Patent No. 3030509, although mass production thereof from natural products was not realized.

The anthocyanidin hydrochloride produced by the synthesis method is stable under strong acidic conditions, however, it is likely to be degraded as compared to a glycoside in weak acidic to neutral regions. The application range was thus very narrow. Accordingly, production of anthocyanin which was more stable in acidic to neutral regions as crystals was awaited, although mass production of anthocyanin by the organic synthesis process is currently still unavailable.

Features of anthocyanins are listed in the Dictionary of Natural Products (issued by Chapman & Hall, 1994, London). For example, the crystal of D3R has not been heretofore reported, and while the crystal form of D3G hydrochloride has been reported, its melting point is not described. This indicates that mass production thereof was difficult. Similarly, although the melting point and the crystal form of C3R hydrochloride are described, there is no description on the melting point of C3G hydrochloride. This indicates that mass production thereof was also difficult. Up to the present, only a very small amount of purified anthocyanin could be produced, regardless of whether it is crystalline or not. Thus, there was substantially no study which investigated the reactivity of various enzymes to anthocyanin. Especially, there was no description on the reactivity of rhamnosidase to anthocyanin. Accordingly, a process for mass producing highly purified anthocyanin from natural products without using complicated synthesis processes has been awaited. Further, a process for mass producing crystalline anthocyanin salts by crystallizing purified anthocyanin was also awaited.

SUMMARY OF THE INVENTION

One aspect of the present invention relates to a process for producing purified anthocyanin in which a rhamnose end of anthocyanidin rutinoside is cleaved using rhamnosidase to convert the anthocyanidin rutinoside component into anthocyanidin glucoside, the anthocyanidin glucoside component being then purified and isolated, or a process for producing crystalline anthocyanidin glucoside salt hydrate by further crystallizing the purified anthocyanin.

Another aspect of the present invention relates to a process for producing purified anthocyanin in which a glucose end of anthocyanidin glucoside is cleaved using β-glucosidase to degrade and remove the end, the anthocyanidin rutinoside component being then purified and isolated, or a process for producing crystalline anthocyanidin rutinoside salt hydrate by further crystallizing the purified anthocyanin.

A further aspect of the present invention relates to a crystalline anthocyanin salt hydrate prepared by these production processes.

More specifically, the first invention provides a process for producing purified anthocyanidin glucoside, wherein rhamnosidase is allowed to act upon an anthocyanin composition containing at least one kind of anthocyanidin rutinoside, and anthocyanidin rutinoside is subjected to hydrolysis to convert into anthocyanidin glucoside, which is then isolated and purified.

The second invention provide a process for producing purified anthocyanidin rutinoside, wherein β-glucosidase is allowed to act upon an anthocyanin composition containing at least one kind of anthocyanidin glucoside and anthocyanidin rutinoside, and anthocyanidin glucoside is subjected to hydrolysis to reduce the anthocyanidin glucoside, the anthocyanidin rutinoside being then isolated and purified.

In the aforementioned first and second inventions, the anthocyanin composition includes fruit juice obtained from at least one member selected from black currant, fig, coffee, banana, blackberry, and the like, and/or an anthocyanin concentrate obtained from wild rice (Zizania aquatica Linn.), colocasia, and the like. The rhamnosidase includes hesperidinase, naringinase and the like. Further, the β-glucosidase can selectively degrade only the β-glucoside bond of anthocyanidin glucoside without degrading the β-glucoside bond of anthocyanidin rutinoside, and specific examples thereof include β-glucosidase derived from almond.

The third invention provides a process for producing crystalline anthocyanidin-3-O-glucoside hydrochloride hydrate through the steps of:

a) allowing rhamnosidase to act upon an anthocyanin composition containing at least one kind of anthocyanidin rutinoside and subjecting anthocyanidin rutinoside to hydrolysis to convert into anthocyanidin glucoside;

b) purifying the anthocyanidin glucoside to obtain anthocyanidin glucoside of 99% or higher purity; and c) crystallizing the anthocyanidin glucoside using a mixed solvent of hydrochloric acid/alcohol system.

The fourth invention provides a crystalline anthocyanidin-3-O-glucoside hydrochloride hydrate obtained by the method according to the third invention.

The fifth invention provides a process for producing crystalline anthocyanidin-3-0rutinoside hydrochloride hydrate through the steps of:

a) allowing β-glucosidase to act upon an anthocyanin composition containing at least one kind of anthocyanidin glucoside and anthocyanidin rutinoside, and subjecting anthocyanidin glucoside to hydrolysis to reduce the anthocyanidin glucoside;

b) purifying the anthocyanidin rutinoside to obtain anthocyanidin rutinoside of 99% or higher purity; and c) crystallizing the anthocyanidin rutinoside using a mixed solvent of hydrochloric acid/alcohol system.

The sixth invention provides a crystalline anthocyanidin-3-O-rutinoside hydrochloride hydrate obtained by the method according to the fifth invention.

In the third and the fifth inventions, the purification process according to step b) can be carried out by ion exchange adsorption chromatography and/or HPLC, and the mixed solvent of hydrochloric acid/alcohol system used in step c) can be composed of 5% (v/v) hydrochloric acid/95% (v/v) methanol.

The seventh invention provides a crystalline delphinidin-3-O-glucoside hydrochloride 0.5 hydrate having the following physical properties:

Melting point based on thermoanalysis: 258° C. Uvλ max(ε): 517 nm (27500) FAB-MS m/z:M$^+$:465

| Compositional formula: | $C_{21}H_{21}O_{12}Cl \cdot 0.5H_2O$ | | |
|---|---|---|---|
| Elementary analysis: | C | H | Cl |
| Measured values: | 48.00 | 4.50 | 6.80 |

The eighth invention provides a crystalline cyanidin-3-O-glucoside hydrochloride 0.5 hydrate having the following physical properties:

Melting point based on thermoanalysis: 245° C. Uvλ max(ε): 510 nm (26300) FAB-MS m/z:M$^+$:449

| Compositional formula: | $C_{21}H_{21}O_{11}Cl \cdot 0.5H_2O$ | | |
|---|---|---|---|
| Elementary analysis: | C | H | Cl |
| Measured values: | 48.80 | 4.70 | 6.90 |

The ninth invention provides a crystalline delphinidin-3-O-rutinoside hydrochloride 1.5 hydrate having the following physical properties:
Melting point based on thermoanalysis: 224° C. Uvλ max(ε):520 nm (27800) FAB-MS m/z M$^+$:611

| Compositional formula: | $C_{27}H_{31}O_{16}Cl \cdot 1.5H_2O$ | | |
|---|---|---|---|
| Elementary analysis: | C | H | Cl |
| Measured values: | 45.80 | 5.30 | 5.20 |

The tenth invention provides a crystalline cyanidin-3-O-rutinoside hydrochloride 0.5 hydrate having the following physical properties:
Melting point based on thermoanalysis: 214 to 226° C. Uvλ max(ε):512 nm (27400) FAB-MS m/z: M$^+$:595

| Compositional formula: | $C_{27}H_{31}O_{15}Cl \cdot 0.5H_2O$ | | |
|---|---|---|---|
| Elementary analysis: | C | H | Cl |
| Measured values: | 50.00 | 5.30 | 5.30 |

The term "anthocyanin" used herein refers to a glycoside which was prepared by the binding of saccharides to anthocyanidin, i.e., an aglycon, and examples thereof include glucoside, rutinoside, arabinoside, and galactoside to which saccharides such as glucose, rutinose, arabinose, and galactose have been bonded.

In the present invention, anthocyanin compositions containing at least one kind of anthocyanidin glucoside and/or anthocyanidin rutinoside that are used in the enzyme reaction may be any substances which contain anthocyanin. Examples thereof include commercially available fruit juice, concentrated juice, beverages, pigment solutions, and powders which are starting materials for foods, pharmaceuticals, or the like. Preferably, concentrated juice is fruit juice obtained from at least one member selected from black currant, fig, coffee, banana, blackberry, and the like, and/or an anthocyanin concentrate which is obtained from wild rice (Zizania aquatica Linn.), colocasia, and the like. The powders are first dissolved in water, buffer, or the like to use the solution in the reaction. More preferably, compositions containing anthocyanin at high levels which are prepared by the method reported in WO 01/01798 by the present inventors are used. Since acids, saccharides, polyphenols, and the like are previously removed, operation in the purification step after the enzyme reaction is facilitated.

The types of aglycon of anthocyanin used for the process for producing purified anthocyanin according to the present invention are not particularly limited. Black currant-derived anthocyanins and salts thereof are preferred. An aglycon moiety of the black currant-derived anthocyanin consists only of delphinidin and cyanidin. In the enzyme reaction, however, these two types are not considered to be particularly specific for anthocyanidin, and can be applied to a glycoside of another anthocyanidin, for example, glycosides such as malvidin, pelargonidin, petunidin, and peonidin represented by formula (I). Further, the black currant-derived anthocyanin component is constituted by four components: cyanidin-3-O-glucoside (C3G), cyanidin-3-O-rutinoside (C3R), delphinidin-3-O-glucoside (D3G), and delphinidin-3-O-rutinoside (D3R).

The types of salts which constitute crystalline anthocyanin salt include salts with mineral acids such as hydrochloric acid and sulfuric acid and salts with organic acids (flavinium salt) such as phosphoric acid, trifluoroacetic acid (TFA), and acetic acid. From the viewpoint of easy crystallization, salts with hydrochloric acid, TFA, and phosphoric acid are preferable.

Rhamnosidase that is used in the present invention is not particularly limited, and it may originate from animals, plants, microorganisms, and the like as long as it has α-rhamnosidase activities at the anthocyanin end as the action mechanism. However, it is important that it has low β-glucosidase activities. Further, anthocyanin is known to be degraded when it is allowed to stand in neutral to basic regions for a long period of time, and its degradation is accelerated by heating. Accordingly, it is necessary that the activity level is high at pH 4.0 or below and at 40° C. or below. Preferable examples thereof include hesperidinase or naringinase, with hesperidinase being more preferred. Hesperidinase includes *Aspergillus niger*-derived substances which are industrially produced for the purpose of degrading hesperidin, which is an opaque white component of Satsuma mandarins. The reactivity of *Aspergillus niger*-derived hesperidinase to anthocyanin has not been heretofore known. Naringinase also includes *Aspergillus niger*-derived substances which are used for taste improvement by degrading naringin, which is a bitter principle from abscised oranges or Citrus aurantium (natsu-mikan). It should be noted that the application of *Aspergillus niger*-derived naringinase to anthocyanin has not been reported.

The source of the β-glucosidase that is used in the present invention is not particularly limited. It must react with anthocyanin and it should have a substrate specificity to degrade only the β-glucoside bond of anthocyanidin glucoside without degrading the β-glucoside bond of anthocyanidin rutinoside. Specifically, suitable β-glucosidase reacts with only terminal glucose but it does not react with glucose which is present at the center in the molecule. As with rhamnosidase, the activity level should be high at pH 4.0 or below and at 40° C. or below, and preferable examples thereof include almond-derived β-glucosidase. While the almond-derived β-glucosidase is a representative β-glucosidase, there has been no study which investigated the reactivity to anthocyanin.

Examples of treatments utilizing the reaction of β-glucosidase to anthocyanin include the conventional use of anthocyanase, which is a type of β-glucosidase, for decolorization and debittering in the fruit juice industry for grape juice and peach nectar and the like, and in the wine industry for wines and sparkling wines including champagnes. However, anthocyanase reacts with and degrades both glucoside and rutinoside of anthocyanin. Thus, it is not suitable for the production of purified anthocyanin.

The reaction conditions which allow these enzymes to act on anthocyanin are not particularly limited. As described above, anthocyanin is known to be degraded when it is allowed to stand in neutral to basic regions for a long period of time and its degradation is accelerated by high temperature. Thus, an acidic region is preferable, and preferably, it is not reacted at high temperature. Specifically, reaction at pH 4.0 or below and at 40° C. or below is likely to be most preferable.

The substrate concentration in the anthocyanin-containing substance that is used in the enzyme reaction is not particularly limited. When the concentration is extremely high, the viscosity of the reaction solution increases and the reaction speed is lowered. Due to a fear of inhibitory reaction by substances in the reaction solution or transition reaction to a substrate, the substrate concentration is preferably 10% (w/v) or below, and more preferably 5% (w/v) or below. The amount of enzymes added is not particularly limited in relation to the reaction time.

After the content of a substrate in the anthocyanin-containing substance, i.e., anthocyanidin rutinoside or anthocyanidin glucoside, is decreased by the enzyme reaction using rhamnosidase or β-glucosidase, the enzyme reaction can be terminated by commonly employed methods, and examples thereof include raising the temperature by heating, pH adjustment by adding acid or alkali, and addition of organic solvent. As described above, anthocyanins are unstable in neutral to basic regions and their degradation is accelerated by heating. Thus, the enzyme reaction is preferably terminated by pH lowering with the addition of strong acids such as hydrochloric acid, TFA, and phosphoric acid or by the addition of organic solvent such as methanol.

In the present invention, purification after the completion of the enzyme reaction can be carried out by column chromatography as well as by a suitable combination of another chromatography, resin adsorption, membrane separation, and the like, if necessary. Of all the methods, chromatography using ODS-silica gel is most preferable. If necessary, the anthocyanin component may be first adsorbed on a cation exchange resin or the like and then eluted in order to similarly purify the prepurified one.

The anthocyanin content herein is determined by summing the contents of each of the anthocyanin components contained, which are calculated by the peak area ratio of anthocyanin by HPLC, as with the disclosure in PCT/JP 00/09204 and WO 01/01798.

Specifically, an anthocyanin sample with a known weight is first analyzed by HPLC and the calibration curve is prepared based on the peak area at 520 nm, to thereby determine the content of each anthocyanin component. Further, the content of each of the components is divided by the peak area to determine the response coefficient, i.e., the mg/peak area. Subsequently, the anthocyanin-containing sample is subjected to HPLC analysis, the response coefficient which was determined from the sample is multiplied by the peak area of each component to calculate the content of each component. Thus, the anthocyanin purity is determined as % by weight (w/w) based on the ratio with the amount injected. Accordingly, the purity of anthocyanin is calculated by including the amount of a bound saccharide in addition to the amount of anthocyanidin, i.e., an aglycon. The purity level of the purified anthocyanin according to the present invention is 99% or higher based on the HPLC analysis.

The crystallization process according to the present invention is preferably carried out mainly from an organic solvent, and methanol is preferably used as the crystallizing solvent. Because anthocyanins are crystallized by generating salts with acids, the addition of acids in the crystallizing solvent is preferred. Preferably, about 1% to 5% (v/v) of hydrochloric acid, TFA, phosphoric acid, or the like is added.

The crystalline D3C, crystalline D3R, crystalline C3G, and crystalline C3R which were prepared in Example 1 or 3 below were subjected to thermoanalysis, and the results thereof are provided below.

The melting point of D3G is 258° C., that of D3R is 224° C., that of C3G is 245° C., and that of C3R is 214 to 226° C.

The crystalline anthocyanin salt according to the present invention is crystal having 99% or higher purity based on the polarization microscopy, elementary analysis, melting point determination, and HPLC analysis, and is a very stable substance without hygroscopicity and with a melting point of 200° C. or higher.

In the past, highly purified anthocyanin or crystalline anthocyanin salt could not be produced. With the use of the production process according to the present invention, however, highly purified anthocyanin and crystalline anthocyanin salt could be produced through purification from natural products. The thus produced crystalline anthocyanin salts did not exhibit any hygroscopicity and were stable.

BEST MODE FOR CARRING OUT THE INVENTION

The present invention will be described in more detail with reference to the following examples, reference examples, and comparative examples. The technical scope of the present invention, however, is not limited by these examples.

REFERENCE EXAMPLE 1

Preparation of Composition Containing Anthocyanin at High Level

In accordance with the process as described in WO 01/01798, compositions containing anthocyanin at high level were prepared. Specifically, 3 kg of commercially available concentrated black currant juice (the anthocyanin purity per solid content: 2.8%) was diluted with water to prepare diluted fruit juice with a concentration of Bx 10. The diluted fruit juice was filtered with a filter paper to remove foreign matter. Thereafter, membrane separation was carried out using a membrane separator (NTR-7410, Nitto Denko Co., Ltd.). The concentrated liquid obtained by membrane separation was spray dried to obtain a powdery composition containing anthocyanin at high level. The anthocyanin purity of this composition was 14.1% per solid content. This composition exhibited hygroscopicity when it was allowed to stand at room temperature.

EXAMPLE 1

Production of Purified delphinidin-3-O-glucoside and Purified cyanidin-3-O-glucoside Using Hesperidinase The powder obtained in Reference Example 1 (40 g) (anthocyanin purity: 14.1%; proportion of each anthocyanin component: 12.5%, 47.9%, 4.1%, and 35.5% for D3G, D3R, C3G, and C3R, respectively) was dissolved in 1 liter of 50 mM acetate buffer (pH 3.5) to prepare an anthocyanin substrate solution. The calculated anthocyanin content in the substrate solution was 5.64 g, and the contents of D3G, D3R, C3G, and C3R were 0.71 g, 2.70 g, 0.23 g, and 2.00 g respectively.

Separately, 79.35 g of hesperidinase (tradename: Hesperidinase Tanabe 2, Tanabe Seiyaku Co,. Ltd) was dissolved in 1 liter of 50 mM acetate buffer (pH 3.5) to prepare an enzyme solution (corresponding to the rhamnosidase activity of 42.5 U/ml).

The substrate solution and the enzyme solution were respectively heated at 40° C. and were then mixed to initiate the reaction. The reaction was carried out at 40° C. for 6 hours, and 2 liters of 3% (w/v) phosphoric acid solution was added to terminate the reaction. Subsequently, 4 liters of ion exchange resin XAD-7 (Rohm and Haas Company) was filled into a column (13 cm (inside diameter)×30 cm (length)), and the reaction mixture (4 liters) was passed therethrough to allow the anthocyanin component to adsorb thereon. Subsequently, 0.1% (w/v) TFA (2 liters) was allowed to pass therethrough to wash the nonadsorbed component. Further, an 80% (v/v) aqueous methanol solution containing 0.1% TFA was passed therethrough to eluate the adsorbed component. This methanol solution was concentrated using a rotary evaporator and converted into an aqueous 3% phosphoric acid solution to bring the concentration of the solid content to 10% (w/v). Thus, a concentrated liquid was obtained.

This concentrated liquid was detected using an ODS-120T silica gel column (ED 5.5×30 cm, 20 μm, TOSOH CORPORATION) with an aqueous 9% (v/v) acetonitrile solution containing 0.1% TFA at a flow rate of 80 ml/min at a wavelength of 520 nm to obtain the D3G fraction with a retention time (R.T.) of 66 to 90 min and the C3G fraction with an R.T. of 158 to 200 min. These fractions has a single peak based on the HPLC analysis, and purified delphinidin-3-O-glucoside and purified cyanidin-3-O-glucoside with a purity level of 99% or higher could be obtained.

Conditions for the HPLC analysis to measure the purity are as follows. Specifically, the analysis was performed under the following gradient conditions using the Hewlett Packard Series 1100 HPLC System (Yokogawa Analytical Systems Inc.).

HPLC Gradient Conditions:

| Time (min) | Liquid A (aqueous 0.5% phosphoric acid solution) | Liquid B (methanol) |
| --- | --- | --- |
| 0 | 80 | 20 |
| 15 | 77 | 23 |
| 20 | 77 | 23 |
| 30 | 50 | 50 |
| 40 | 50 | 50 |

A Zorbax SB-C18 column (4.6 mm×250 nm, 5 μm, Hewlett Packard) was used. Detection was carried out at the flow rate of 1 ml/min at the wavelength of 520 nm. The R.T.s of the sample D3G and C3G were respectively 10.54 min and 14.60 min.

A part of the substrate solution before the enzyme reaction and a part of the solution in which the enzyme reaction was terminated were collected, and foreign matters were removed through a microfilter with a pore diameter of 0.45 μm to prepare an anthocyanidin glucoside solution. The contents of anthocyanin components before the reaction and after the reaction were measured. The results are as shown in Table 1. The results indicate that the substrate solution consisted only of anthocyanidin glucoside because anthocyanidin rutinoside was degraded and anthocyanidin glucoside was generated in the substrate solution. In addition, the amount of D3G was 3.36 times higher than before the reaction, and the amount of C3G was 6.78 times higher than before the reaction.

TABLE 1

Change in anthocyanin content

|  | D3G | D3R | C3G | C3R |
| --- | --- | --- | --- | --- |
| Before reaction | 0.71 g | 2.70 g | 0.23 g | 2.00 g |
| After reaction | 2.39 g | 0.00 g | 1.56 g | 0.00 g |

EXAMPLE 2

Production of Crystalline delphinidin-3-O-glucoside Hydrochloride Hydrate and Crystalline cyanidin-3-O-glucoside hydrochloride Hydrate The D3G fraction and C3G fraction obtained in Example 1 were concentrated using a rotary evaporator, and 30 ml of heptane was added thereto, followed by reconcentration to dryness. TFA which was included during the separation operation was removed. The result of weight measurement showed the obtained D3G fraction was 1.51 g and the C3G fraction was 0.98 g.

The D3G fraction and the C3G fraction were separately dissolved in 5% hydrochloric acid/95% methanol, and were then allowed to stand at 5° C. for 24 hours to perform crystallization. Solid liquid separation was carried out using the Kiriyama funnel and No. 2 filter paper (Whatman), and washing with a small amount of acetone was carried out, followed by drying to obtain precipitates. Both of the obtained precipitates were observed under a polarization microscope, and polarization of light was observed. This indicated that they were in crystal forms. The yield of crystalline D3G hydrochloride was 1.06 g and that of crystalline C3G hydrochloride was 0.59 g.

The structures of the crystalline D3G hydrochloride and the crystalline C3G hydrochloride obtained were determined by NMR. The structures of these two types of anthocyanins were consistent with the spectrum data which have been already reported.

Other physical properties of the crystalline D3G hydrochloride and the crystalline C3G hydrochloride are as follows.

Crystalline D3G hydrochloride:

Melting point based on thermoanalysis: 258° C. Uvλ max(ε): 517 nm (27500) FAB-MS m/z: M$^+$:465

| Compositional formula: | $C_{21}H_{21}O_{12}Cl \cdot 0.5H_2O$ | | |
| --- | --- | --- | --- |
| | Elementary analysis: | | |
| | C | H | Cl |
| Measured values: | 48.00 | 4.50 | 6.80 |
| Calculated values | 47.78 | 4.58 | 6.72 |

Crystalline C3G hydrochloride:

Melting point based on thermoanalysis: 245° C. Uvλ max(ε): 510 nm (26300) FAB-MS m/z: M$^+$:449

| Compositional formula: | $C_{21}H_{21}O_{11}Cl \cdot 0.5H_2O$ | | |
| --- | --- | --- | --- |
| | Elementary analysis: | | |
| | C | H | Cl |
| Measured values: | 48.80 | 4.70 | 6.90 |
| Calculated values: | 49.57 | 4.73 | 6.93 |

EXAMPLE 3

Production of Purified delphinidin-3-O-rutinoside and Purified cyanidin-3-O-rutinoside Using Almond-Derived β-glucosidase The powder (3.42 g) obtained in Reference Example 1 was dissolved in 1 liter of 50 mM acetate buffer (pH 3.5) to prepare an anthocyanin substrate solution.

Separately, 208 g of almond-derived 0-glucosidase (SIGMA) was dissolved in 1 liter of 50 mM acetate buffer (pH 3.5) to prepare an enzyme solution (corresponding to 500 U/ml). The substrate solution (1 liter) was heated at 40° C. for 10 minutes to stabilize the temperature. Thereafter, 1 liter of enzyme solution was added and thoroughly stirred to initiate the reaction. Sixty minutes later, 2 liters of 0.3N hydrochloric acid was added to terminate the reaction.

Subsequently, 4 liters of reaction mixture, in which the reaction was terminated, was treated by the adsorption of an ion exchange resin in the same manner as described in Example 1, and further purified by HPLC using an ODS-silica gel column. Thus, a D3R fraction with an R.T. of 69 to 96 minutes and a C3R fraction with an R.T. of 144 to 174 minutes were obtained.

These fractions were analyzed under the HPLC analysis conditions as described in Example 1 (the R.T.s of the sample D3R and C3R were 12.63 minutes and 18.19 minutes, respectively). The results showed that the D3R fraction and the C3R fraction had a single peak. Thus, purified delphinidin-3-o-rutinoside and purified cyanidin-3-O-rutinoside having a purity level of 99% or higher could be obtained.

The anthocyanin contents in the substrate solution before the reaction and that in the solution after the reaction which were measured by HPLC are shown in Table 2. According to Table 2, only anthocyanidin glucoside was degraded and most of anthocyanidin rutinoside remained undegraded. This indicates that a reaction solution having an optimal composition for purification was obtained.

TABLE 2

Change in anthocyanin content

|  | D3G | D3R | C3G | C3R |
|---|---|---|---|---|
| Before reaction | 60.3 mg | 231 mg | 19.8 mg | 171 mg |
| After reaction | 5.6 mg | 207 mg | 0.0 mg | 162 mg |

EXAMPLE 4

Production of Crystalline delphinidin-3-O-rutinoside Hydrochloride Hydrate and Crystalline Cyanidin-3-O-rutinoside Hydrochloride Hydrate Precipitates were obtained through the crystallization process as with Example 2. Both the obtained precipitates were observed under a polarization microscope, and as a result, polarization of light was observed and they were found to be in crystal forms. The yield of crystalline C3R hydrochloride was 58 mg and that of crystalline D3R hydrochloride was 88 mg.

The structures of the crystalline D3R hydrochloride and the crystalline C3R hydrochloride obtained were determined by NMR. The structures of these two types of anthocyanins were consistent with the spectrum data which have been already reported.

Physical properties of the crystalline D3R hydrochloride and the crystalline C3R hydrochloride are as follows.

Crystalline D3R hydrochloride:

Melting point based on thermoanalysis: 224° C. Uvλ max(ε): 520 nm (27800) FAB-MS m/z: M$^+$:611

| Compositional formula: | $C_{27}H_{31}O_{16}Cl \cdot 1.5H_2O$ | | |
|---|---|---|---|
| | Elementary analysis: | | |
| | C | H | Cl |
| Measured values: | 45.80 | 5.30 | 5.20 |
| Calculated value: | 45.86 | 5.38 | 4.98 |

Crystalline C3R hydrochloride:

Melting point based on thermoanalysis: 214 to 226° C. Uvλ max(ε): 512 nm (27400) FAB-MS m/z: M$^+$:595

| Compositional formula: $C_{27}H_{31}O_{15}Cl \cdot 0.5H_2O$ | | | |
|---|---|---|---|
| | Elementary analysis: | | |
| | C | H | Cl |
| Measured values: | 50.00 | 5.30 | 5.30 |
| Calculated values: | 49.97 | 5.13 | 5.46 |

COMPARATIVE EXAMPLE 1

Enzyme Reaction Using Commercially Available Anthocyanase

The powder (342 mg) obtained in Reference Example 1 was dissolved in 100 ml of 50 mM acetate buffer (pH 3.5) to prepare an anthocyanin substrate solution.

Separately, CYTOLASE PCL5 (tradename, GIST-brocades), which is a type of representative anthocyanase used in the fruit juice industry, was diluted to 10-fold with a 50 mM acetate buffer (pH 3.5) to obtain an enzyme solution.

The substrate solution (2 ml) was heated at 40° C. for 10 minutes to stabilize the temperature. Thereafter, 2 ml of enzyme solution was added and thoroughly stirred to initiate the reaction. Fifteen minutes later, 200 μl of a reaction solution was sampled, and 200 μl of 0.3N hydrochloric acid was added to terminate the reaction.

The anthocyanin compositions before the reaction and after the reaction were measured by HPLC. The anthocyanin contents and compositions before and after the reaction are shown in Table 3 below. Table 3 shows that both the anthocyanidin glucoside and the anthocyanidin rutinoside were degraded, indicating the composition was unsuitable for purification of anthocyanin glycoside.

TABLE 3

Change in anthocyanin content

|  | D3G | D3R | C3G | C3R |
|---|---|---|---|---|
| Before reaction | 0.60 mg | 2.31 mg | 0.20 mg | 1.71 mg |
| After reaction | 0.23 mg | 0.09 mg | 0.26 mg | 0.04 mg |

INDUSTRIAL APPLICABILITY

The present invention enabled the production of highly purified anthocyanin and crystalline anthocyanin salt through purification from natural products. The thus produced crystalline anthocyanin salt did not exhibit hygroscopicity and was stable.

This specification includes part or all of the contents as disclosed in the specification of Japanese Patent Application No. 2000-276540, which is a priority document of the present application. All publications, patents and patent applications cited herein are incorporated herein by reference in their entirety.

The invention claimed is:

1. A process for producing purified anthocyanidin glucoside, wherein rhamnosidase is contacted with an anthocyanin composition containing at least one anthocyanidin rutinoside to convert the anthocyanidin rutinoside into anthocyanidin glucoside, which is then isolated and purified.

2. The process for producing purified anthocyanidin glucoside according to claim 1, wherein the anthocyanin composition is fruit juice obtained from at least one member selected from black currant, fig, coffee, banana, and blackberry and/or an anthocyanin concentrate obtained from wild rice (*Zizania aquatica* Linn.) or colocasia.

3. The process for producing purified anthocyanidin glucoside according to claim 1, wherein the rhamnosidase is hesperidinase or naringinase.

4. A process for producing crystalline anthocyanidin-3-O-glucoside hydrochloride hydrate comprising:
   a) contacting rhamnosidase with an anthocyanin composition containing at least one anthocyanidin rutinoside to convert the anthocyanidin rutinoside into anthocyanidin glucoside;
   b) purifying the anthocyanidin glucoside to obtain anthocyanidin glucoside of 99% or higher purity; and
   c) crystallizing the anthocyanidin glucoside of 99% or higher purity using a mixed solvent of hydrochloric acid/alcohol system to obtain crystalline anthocyanidin-3-O-glucoside hydrochloride hydrate.

5. The process for producing crystalline anthocyanidin-3-O-glucoside hydrochloride hydrate according to claim 4, wherein the purification process according to step b) in claim 4 is carried out by ion exchange adsorption chromatography and/or HPLC.

6. The process for producing crystalline anthocyanidin-3-O-glucoside hydrochloride hydrate according to claim 4, wherein the mixed solvent of hydrochloric acid/alcohol system is composed of 5% (v/v) hydrochloric acid /95% (v/v) methanol.

7. The process for producing purified anthocyanidin glucoside according to claim 2, wherein the rhamnosidase is hesperidinase or naringinase.

* * * * *